(12) United States Patent
Hamann et al.

(10) Patent No.: US 8,268,856 B2
(45) Date of Patent: Sep. 18, 2012

(54) METHOD TO USE COMPOSITIONS HAVING ANTIDEPRESSANT ANXIOLYTIC AND OTHER NEUROLOGICAL ACTIVITY AND COMPOSITIONS OF MATTER

(76) Inventors: Mark T. Hamann, Oxford, MS (US); Anna J. Kochanowska, Oxford, MS (US); Abir El-Alfy, Oxford, MS (US); Rae R. Matsumoto, Morgantown, WV (US); Angelo Boujos, Pickering (CA)

(*) Notice: Subject to any disclaimer, the term of this patent is extended or adjusted under 35 U.S.C. 154(b) by 0 days.

(21) Appl. No.: 13/253,958

(22) Filed: Oct. 5, 2011

(65) Prior Publication Data

US 2012/0029010 A1 Feb. 2, 2012

Related U.S. Application Data

(63) Continuation of application No. 12/248,234, filed on Oct. 9, 2008, now abandoned.

(60) Provisional application No. 61/090,484, filed on Aug. 20, 2008, provisional application No. 60/978,756, filed on Oct. 9, 2007.

(51) Int. Cl.
*A61K 31/4375* (2006.01)
*A61K 31/4045* (2006.01)
*A61K 31/137* (2006.01)
*C07D 471/04* (2006.01)
*A61P 25/24* (2006.01)
*A61P 25/22* (2006.01)

(52) U.S. Cl. .......................................... 514/292; 546/88

(58) Field of Classification Search .................. None
See application file for complete search history.

(56) References Cited

OTHER PUBLICATIONS

Guillier et al. in Journal of Heterocyclic Chemistry (1999), 36(5), 1157-1165.*

* cited by examiner

*Primary Examiner* — Brandon Fetterolf
*Assistant Examiner* — Dennis Heyer
(74) *Attorney, Agent, or Firm* — Harris, Shelton, Hanover & Walsh

(57) ABSTRACT

The sponges were collected from a variety of locations in the Florida Keys and separated based on morphology and color. The samples were identified as three species, two of which are well known: *V. rigida* (Esper, 1794) (order Verongida, family Aplysinidae) and *S. aurea* (Hyatt, 1875) (order Dictyoceratida, family Thorectidae), and a third *S. cerebriformis* (Duchassaing & Michelotti, 1864), is less common and separated based on subtle differences of morphology and coloration, from the other two species. Several compounds were isolated and were evaluated in established animal models predictive of neurological related drug function, namely, the rodent FST and the chick anxiety-depression model.

2 Claims, 12 Drawing Sheets

R₁=R₂=CH₃
R₁=R₂=H
R₁=H, R₂=CH₃
R₁=R₂=CH₂CH₃
R₁=R₂=iPro

R₁=R₂=R₃=H
R₁=H, R₂=R₃=CH₃
R₁=R₂=R₃=CH₃
R₁=CH₃, R₂=R₃=H
R₁=CH₃, R₂=R₃=CH₂CH₃

R₁=Br
R₁=Cl
R₁=F

METHOD TO USE COMPOSITIONS HAVING ANTIDEPRESSANT ANXIOLYTIC AND OTHER NEUROLOGICAL ACTIVITY AND COMPOSITIONS OF MATTER

RELATED APPLICATIONS

This application is a continuation of U.S. patent application Ser. No. 12/248,234, filed Oct. 9, 2008 now abandoned, which claims the benefit of U.S. Provisional Application No. 61/090,484, filed Aug. 20, 2008, and U.S. Provisional Application No. 60/978,756, filed Oct. 9, 2007, each of which is hereby incorporated by reference herein in its entirety.

STATEMENT REGARDING FEDERALLY SPONSORED RESEARCH OR DEVELOPMENT

This research is supported in part by grants from the National Institute of Health of the United States of America R01A136596 and P20 RR021929. The government of the United States has certain rights in this invention.

BACKGROUND OF THE INVENTION

This invention relates to marine compositions having antidepressant, anxiolytic, antiobesity activity and other neurological applications including migraine and pain control in both veterinary medicine and human health applications.

BRIEF SUMMARY OF THE INVENTION

In one embodiment the subject invention pertains to the use of compounds having the following general structure:

(I)

wherein $R_5$ and $R_6$ are the same or different halogen and the remaining R groups are hydroxy, oxy, halo (Br, Cl, I, Fl), $C_1$-$C_{12}$-alkoxy, $C_1$-$C_{12}$-acyloxy, amide, lower mono or dialkyl amino, aminal, thiol, $C_1$-$C_{12}$-alkylthiol, nitro, $C_1$-$C_{12}$-alkysulfonyl, aminosulfonyl, hydroxyl sulfonyl, $C_1$-$C_{12}$-acylamino, sulphate, $C_1$-$C_{12}$-alkyl, $C_1$-$C_{12}$-acyl or aryl groups. In addition reduction or oxidation of aromatic or olefinic moieties is included as a subject of this invention as well as N-substituted analogs of molecules shown above.

In another embodiment, this invention also relates to haloindole derivatives as depicted by the formula:

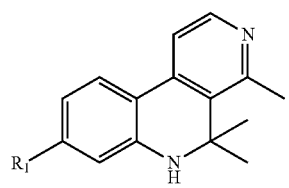

(II)

wherein $R_1$=Br, Cl, I or F.

More specifically, this invention relates to a method for using 5-6-dibromo-N—N-dimethyltryptamine and 5-bromo-N—N-dimethytryptamine as a anxiolytic/antidepressant agent and 5-bromo-N—N-dimethytryptamine as a sedative.

In another embodiment, the invention relates to haloindole derivates as depicted by the formula:

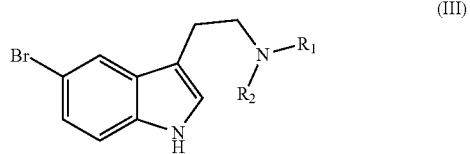

(III)

$R_1 = R_2 = CH_3$
$R_1 = R_2 = H$
$R_1 = H \cdot R_2 = CH_3$
$R_1 = R_2 = CH_2CH_3$
$R_1 = R_2 = i$Pro In another embodiment, the novel compound VR1 Veranamine is disclosed as (8-bromo-4,5,5-trimethyl-5,6-dihydrobenzo[c][2,7]naphthyridine). VR1 is depicted by the formula:

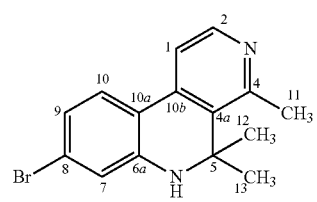

(IV)

This invention also relates to halodopamine derivatives as depicted by the formula:

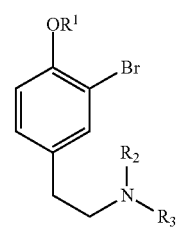

(V)

$R_1 = R_2 = R_3 = H$
$R_1 = H, R_2 = R_3 = CH_3$
$R_1 = R_2 = R_3 = CH_3$
$R_1 = CH_3, R_2 = R_3 = H$
$R_1 = CH_3, R_2 = R_3 = CH_2CH_3$

More specifically, the halodopamine derivative 3-bromotyramine is shown to have antidepressant activity and a sedative effect.

One embodiment of the invention is a pharmaceutical composition or formulation made of a haloindole derivative, its analog, its optical isomer, its racematic form, its tautomeric form, its stereoisomer, or a pharmaceutically acceptable salt thereof, optionally in a mixture with a pharmaceutically acceptable diluent or carrier.

A preferred embodiment is the pharmaceutical formulation of (8-bromo-4,5,5-trimethyl-5,6-dihydrobenzo[c][2,7]naphthyridine), its analog, its optical isomer, its racematic form, its tautomeric form, its stereoisomer, or a pharmaceutically acceptable salt thereof, optionally in a mixture with a pharmaceutically acceptable diluent or carrier.

Another preferred embodiment is the pharmaceutical formulation of 5-Bromo-N,N-dimethyltryptamine or 5-6-dibromo-N—N-dimethyltryptamine, its analog, its optical isomer, its racematic form, its tautomeric form, its stereoisomer, its polymorph or a pharmaceutically acceptable salt or pharmaceutically acceptable solvate thereof, optionally in a mixture with a pharmaceutically acceptable diluent or carrier.

Another embodiment is the pharmaceutical formulation of 2-(3'-bromo-4'hydroxyphenol)-ethanamine, also known as 3-Bromotyramine, its analog, its optical isomer, its racematic form, its tautomeric form, its stereoisomer, its polymorph or a pharmaceutically acceptable salt or pharmaceutically acceptable solvate thereof, optionally in a mixture with a pharmaceutically acceptable diluent or carrier.

A further embodiment of the invention is the treatment of depression, anxiety, obsessive-compulsive disorders, sleep disorders, eating disorders, pain associated with migraines, headache associated with migraine, tension and anxiety or other neuropsychiatric diseases or conditions which comprise administering to a subject suffering from or susceptible to such a disease or condition, a therapeutically effective amount of a haloindole derivative or brominated dopamine derivative or analog, or an optical isomer or racemate or tautomer thereof or a pharmaceutically acceptable salt thereof.

The treatment of depression and anxiety, is an especially preferred embodiment. It is especially preferred that a pharmaceutical formulation made of 5,6-dibromo-N,N-dimethyltryptamine is used in the treatment of depression and anxiety as well as migraine related pain.

DETAILED DESCRIPTION OF THE INVENTION

Figure 1:
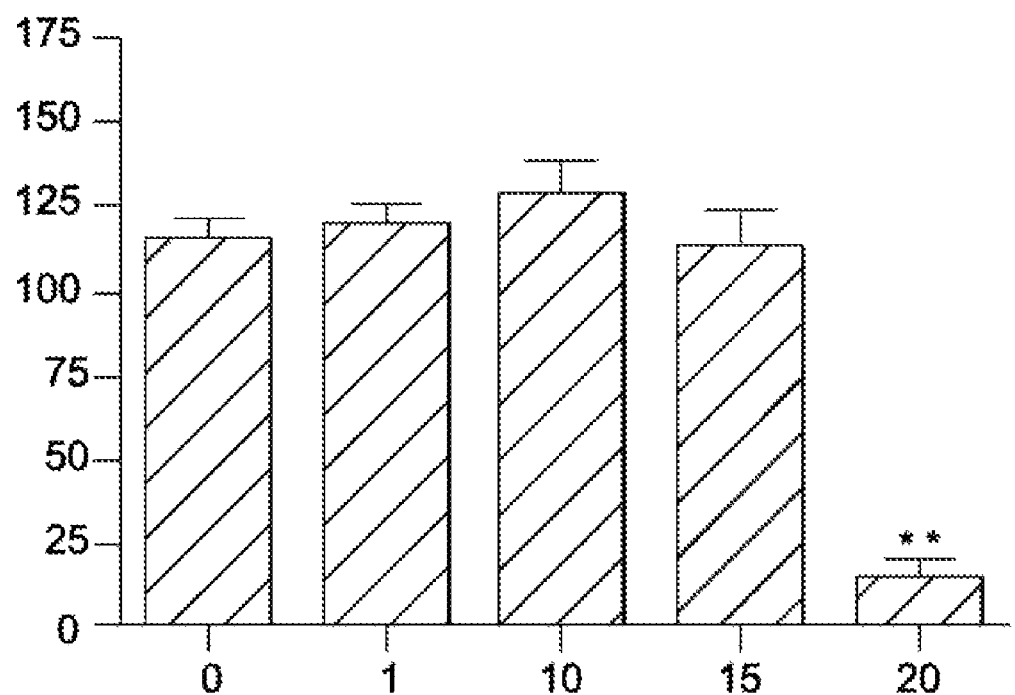
FIG. 1. Shows reduction of immobility time in the FST by 5,6-dibromo-N, N-dimethyltryptamine (mg/kg×axis) (Y axis immobility in seconds).

The present invention provides halogenated indole alkaloid pharmaceutical formulations and composition shown in formulas (II) & (IV) and methods for the use of indole derivatives (e.g. as shown in formula (I) and related compounds (II, III, IV) and a halodopamine derivative (V) as therapeutic agents to treat a number of neurological conditions including depression, anxiety, obsessive-compulsive disorders, sleep disorders, eating disorders, pain associated with migraines, tension and anxiety or other neuropsychiatric diseases or conditions. Marine natural products can be used to treat medical conditions by administering to a subject suffering from or susceptible to such a disease or condition, a therapeutically effective amount of a haloindole or halodopamine compound or a derivative or analog, or an optical isomer or racemate or tautomer thereof or a pharmaceutically acceptable salt thereof or optimally in a mixture with a pharmaceutically acceptable diluent or carrier.

The pharmaceutical formulation or compositions can be administered via any suitable therapeutic method and technique presently or prospectively known to those skilled in the art. Further, the compounds for use in this invention have use as starting materials for the preparation of other useful drug products and compositions.

Skilled chemists having the benefit of the present disclosure including the structure of these haloindoles can use established procedures to prepare the subject compounds from sponge/microbial extracts or through synthetic or biocatalytic methodologies. In carrying out such operations, suitable filtration, chromatographic, crystallization and other purification techniques well known in the art may be used. These techniques may include, for example, reversed phase liquid chromatography (RPLC), column, vacuum flash, medium pressure (MPLC) and high performance liquid chromatography (HPLC) with a suitable column such as silica gel, Sephadex LH-20, ammonia-treated silica gel, bonded phase RP-18, RP-8 and amino columns. Such columns are eluted with suitable solvents such as hexanes, ethyl acetate, acetone, methylene chloride, methanol, isopropanol, acetonitrile, water, trifluoroacetic acid (TFA) ammonium acetate and various combinations thereof.

The dosage administered to a host will be dependent upon the identity of the neuropsychiatric disorder, the type of host involved, its age, weight, health, kind of concurrent treatment, if any, frequency of treatment and therapeutic ratio.

The compounds of the subject invention can be formulated according to known methods for preparing pharmaceutically useful compositions. Formulations are described in detail in a number of sources that are well known and readily available to those skilled in the art. For example, Remington's Pharmaceutical Science by E. W. Martin describes formulations that can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as the active ingredient, an effective amount of one or more of the subject compounds and one or more non-toxic, pharmaceutically acceptable carriers or diluents, can be used by persons of ordinary skill in the art. In addition, the pharmaceutical composition can comprise one or more of the halodindole as a first active ingredient together with a second or third active ingredient comprising an established neuropsychiatric compound known in the art.

The most effective mode of administration and dosage regimen of the compounds as neuropsychiatric agents will depend upon the type of condition to be treated, the severity and course of that condition, previous therapy, the patient's health status and response to drug and the judgment of the treating physician or veterinarian. The natural or synthetic compositions may be administered to the subject at one time or over a series of treatments.

The present pharmaceutical compositions or formulations are made of an indole derivative and include, analog, an optical isomer, racemate, tautomer thereof or a pharmaceutically acceptable salt thereof, optionally in a mixture with a pharmaceutically acceptable diluent or carrier. Further, the invention relates to the treatment of depression, anxiety, obsessive-compulsive disorders, sleep disorders, eating disorders, pain associated with migraines, tension and anxiety or other neuropsychiatric diseases or conditions which comprise administering to a subject suffering from or susceptible to such a disease or condition, a therapeutically effective amount of a haloindole or halodopamine derivative or analog, or an optical isomer or racemate or tautomer thereof or a pharmaceutically acceptable salt thereof.

Any of the identified haloindoles, halotyrosine, or derivatives or analogs can be administered to an animal host, including a human patient, by itself, or in pharmaceutical compositions where it is mixed with suitable carriers or excipient(s) at doses therapeutically effective to treat or ameliorate a variety of neurological diseases and disorders including but not limited to, anxiety, depression, obesity, post-traumatic stress disorder, pain associated with migraines, tension and anxiety, sleep disorders requiring sedation or narcolepsy. Anxiety in animals including, but not limited to, those induced by lightning, thunder and gunfire. Anxiety in performance horses and dogs bred or selected to be anxious and high energy. Depression in domesticated animals as diagnosed based on fatigue and listlessness. Obesity and other common eating disorders in animals and humans. A therapeutically effective dose further refers to that amount of the compound sufficient to result in amelioration of symptoms associated with such disorders.

Techniques for formulation and administration of the compounds of the instant application may be found in "Remington's Pharmaceutical Sciences", Mack Publishing Co. Easton, Pa. latest edition.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from serum levels and behavior assays. For example, a dose can be formulated in animal models to achieve a circulating concentration range that includes the EC50 (the dose where 50% of the subjects show the desired effects) as determined in behavior assays. Such information can be used to more accurately determine useful doses in humans and animals.

A therapeutically effective dose refers to that amount of the compound resulting in amelioration of symptoms or a prolongation of survival in a patient. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio between LD50 and ED50. Compounds that exhibit high therapeutic indices are preferred. The data obtained from the receptor binding assays and animal studies can be used in formulating a range of dosage for use in animal and human subjects. The dosage of such compounds lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's or subject's condition. (See e.g. Fingl et al., 1975, in "The Pharmacological Basis of Therapeutics", Ch. 1 p 1). Dosage amount and interval may be adjusted individually to provide plasma levels of the active moiety that are sufficient to maintain the desired effects.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician. In a preferred embodiment, efficacy ranges from about 0.1 mg/kg to 100 mg/kg daily.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries that facilitate processing of the active compounds into preparations that can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, pellets, dragees, capsules, liquids, gels, syrups, slurries, suspensions and the like, for oral ingestion by a patient to be treated.

Pharmaceutical preparations for oral use can be made as solid excipient, by optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxy-methylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in a conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichloro-fluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion.

Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials as an emulsion in an acceptable oil or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. Naturally, the proportions of a co-solvent system may be varied considerably without destroying its solubility and toxicity characteristics. Furthermore, the identity of the co-solvent components may be varied.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various types of sustained-release materials have been established and are well known by those skilled in the art.

Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The terms: compound, formulation or the specific compounds listed by name can be interpreted to include salts with pharmaceutically compatible counterions. The phrase "pharmaceutically acceptable salts" refers to the relatively non-toxic inorganic and organic acid addition salts, and base addition salts, of the compounds of the present invention. These salts may be prepared in situ during final isolation and purification of the compounds. In particular, the acid addition salts may be prepared by separately reacting the purified compound in its clean form with an organic or inorganic acid and isolating the resultant salt. Examples of acid addition salts include hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptanate, lactobionate, sulfamates, malonates, salicylates, propionates, methylenebis-beta-hydroxynaphthoates, gentisic acid, isethionates, di-p-toluoyltartrates, methanesulfonates, ethanesulfonates, benzenesulfonates, p-toluenesulfonates, cyclohexyl sulfamates and quinate lauryl sulfonate, and the like. (See for example S. M. Berge et al. "Pharmaceutical Salts" J. Pharm. Sci, 66: p. 1-19 (1977) which is incorporated herein by reference). The acid addition salts may also be prepared by separately reacting the purified compound in its acid form with an organic or inorganic base and isolating the resultant salt. Acid addition salts include amine and metal salts. Suitable metal salts comprise the salts of sodium, potassium, calcium, barium, zinc, magnesium and aluminium. Sodium and potassium salts are preferred. Suitable inorganic base addition salts are prepared from metallic bases which comprise sodium hydride, sodium hydroxide, potassium hydroxide, calcium hydroxide, aluminium hydroxide, lithium hydroxide, magnesium hydroxide, zinc hydroxide. Suitable amine base addition salts are prepared from amines which have sufficient alkalinity to form a stable salt, and preferably comprise the amines which are frequently used in medicinal chemistry due to their low toxicity and their acceptability for medical use: ammonia, ethylenediamine, N-methylglucamine, lysine, arginine, ornithine, choline. N,N'-dibenzylethylenediamine, chloroprocaine, diethanolamine, procaine, N-benzylphenethylamine, diethylamine, piperazine, tris(hydroxymethyl)-aminomethane, tetramethylammonium, hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, for example lysine and arginine, and dicyclohexylamine, and the like.

Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

Suitable routes of administration may, for example, include oral, rectal, transmucosal, transdermal, or intestinal administration; parenteral delivery, including intramuscular, subcutaneous, intramedullary injections, as well as intrathecal, direct intraventricular, intravenous, intraperitoneal, intranasal, or intraocular injections. A suitable carrier can include sterile water.

Alternately, one may administer the compound in a local rather than systemic manner, for example, via injection of the compound directly into an affected area, often in a depot or sustained release formulation.

Furthermore, one may administer the drug in a targeted drug delivery system, for example, in a liposome coated with an antibody specific for affected cells. The liposomes will be targeted to and taken up selectively by the cells.

The drugs may also be administered in a prodrug form in which a hydrolysable, oxidizable or reducible moiety has been formed at one or more reactive sites in the molecule. These include but are not limited to esters, sulphates, phosphates or any other group which can be readily metabolized to generate the active form of the drug.

In veterinarian application the pharmaceutical composition can be delivered as a pellet or powder. The inactive ingredient can be, for example, alfalfa, apple flavor, cane molasses, propionic acid, sorbitol, Vitamin E complex and wheat germ meal.

Brominated indole alkaloids are a common class of metabolites reported from sponges of the order Verongida. Herein we report the isolation, structural determination and activity of metabolites from three Florida sponges, namely, *Verongula rigida* (order Verongida, family Aplysinidae), *Smenospongia aurea*, and *S. cerebriformis* (order Dictyoceratida, family Thorectidae). All three species were investigated chemically revealing similarities in secondary metabolites. Brominated compounds, as well as sesquiterpene quinones and hydroquinones were identified from both *V. rigida* and *S. aurea* despite their apparent taxonomic differences at the ordinal level. Isolated compounds were evaluated in the Porsolt FST (FST) and the chick anxiety-depression continuum model. Among the isolated compounds, 5,6-dibromo-N,N-dimethyltryptamine exhibited significant antidepressant-like action in the rodent FST model while 5-bromo-N,N-dimethyltryptamine caused significant reduction of locomotor activity indicative of a potential sedative action.

Example 1

Evaluation of Marine Natural Products

The sponges were collected from a variety of locations in the Florida Keys and separated based on morphology and color. The samples were identified as three species, two of which are well known: *V. rigida* (Esper, 1794) (order Verongida, family Aplysinidae) and *S. aurea* (Hyatt, 1875) (order Dictyoceratida, family Thorectidae), and a third *S. cerebriformis* (Duchassaing & Michelotti, 1864), is less common and separated based on subtle differences of morphology and coloration, from the other two species. Several known compounds were isolated and those that bear structural similarity to serotonin were evaluated in two established animal models predictive of antidepressant drug action, namely, the rodent FST and the chick anxiety-depression model. Exhaustive extraction of 3 kg of *V. rigida* yielded 211 g of crude extract. The fractionation and further purification (described in detail in the Experimental Section) of the crude extract yielded the following known metabolites: 5,6-dibromo-N,N-dimethyltryptamine (1) 5-bromo-N,N-dimethyltryptamine (2), aplysinopsin (3), makaluvamine O (9), arborescidine C (5), 11 6-bromoaplysinopsin (6), 5,6-dibromoabrine (7), and small amounts of aureol (8) and ilimaquinone (4). The ethanol extract of *S. aurea* was purified to yield aureol (8) and four indole alkaloids which were identified as 5,6-dibromo-N—N-dimethyltryptamine (1), 2'-des-N-methylaplysinopsin (10) 6-bromoaplysinopsin (6), and makaluvamine O (9).

All the compounds previously reported from other *Verongida* species were identified by comparison of their spectral data with literature values. Similar patterns of secondary metabolite production were found in species belonging to two distinct orders (Verongida and Dictyoceratida) providing evidence for common microbial source of these compounds.

Four of the isolated compounds were tested in the Porsolt FST (FST) and chick anxiety-depression continuum models. The locomotor activity test was performed to demonstrate that reductions in immobility time shown by the isolated compounds were not a secondary consequence of their non-specific stimulant actions.

Figure 2A:
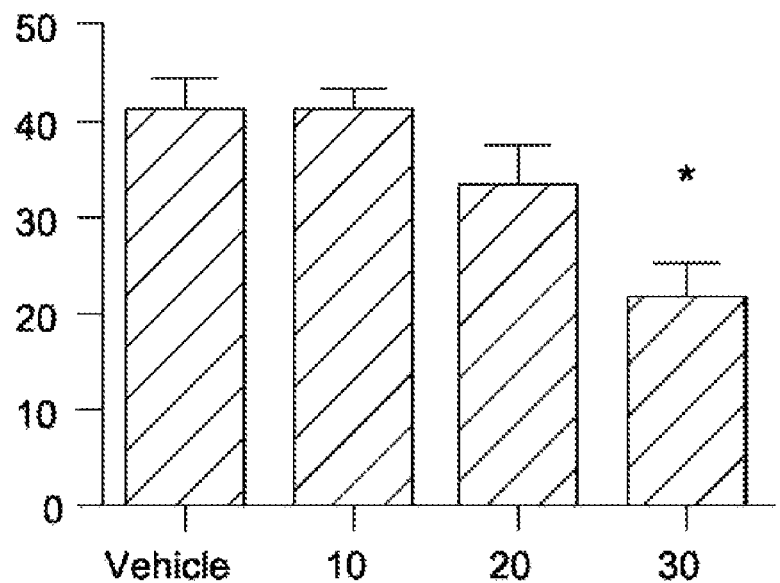
FIG. 2A. Shows the effects of 5,6-dibromo-N,N-dimethyltryptamine on separation distress vocalization rates during the anxiety phase (0 to 5 min).
Figure 2B:
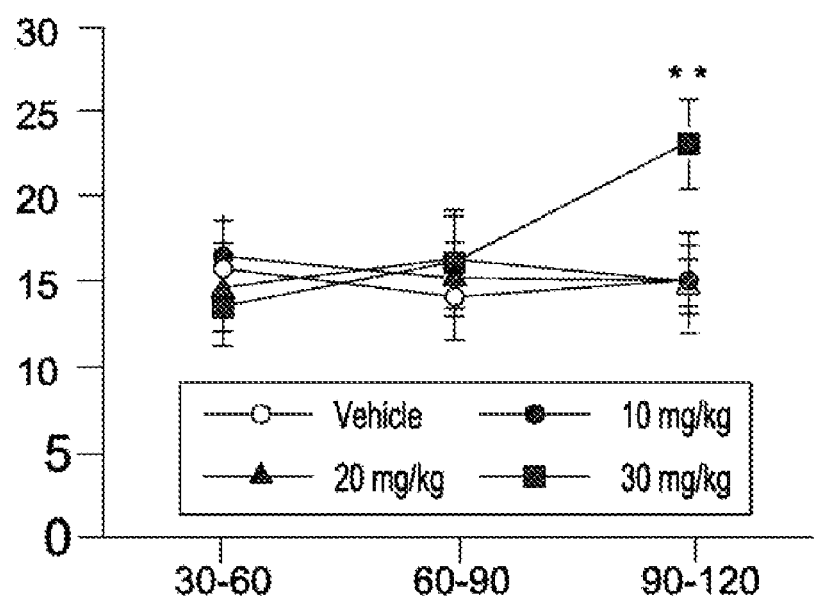
FIG. 2B. Shows the effects of 5,6-dibromo-N,N-dimethyltryptamine on separation distress vocalization rates during the anxiety phase on the depression phase (30 to 120 min, panel B) of the test session. * indicates a significant decrease (i.e., anxiolytic effect) and ** indicates a significant increase (i.e., antidepressant effect) of vocalization rate compared to vehicle-treated chicks. All ps<0.05.

5,6-Dibromo-N,N-dimethyltryptamine (1) was evaluated in the FST and chicken anxiety-depression model. The FST showed (1) possesses significant antidepressant-like activity (F[4.44]=31.56, p<0.01) (FIG. 1). Posthoc comparisons of individual doses to the vehicle control showed that 5,6-Dibromo-N,N-dimethyltryptamine significantly reduced the immobility time only at the 20 mg/kg dose (q=8.28, p<0.01). In the chick anxiety-depression continuum model, socially raised chicks are separated from conspecifics during a two hour test session. Vehicle-treated chicks displayed high rates of vocalizations during the initial 5 min time block that declined over the next 20-25 minute period to approximately 50% of the initial rate and remained stable throughout the remainder of the test session. Previous studies have shown the first 5 min block to model the anxiety phase whereby a diverse set of anxiolytic compounds reduce distress vocalizations and that the last 90 min of the test session models the depressive phase of the model whereby antidepressants increase distress vocalizations (i.e., block the onset of behavioral despair). Sufka, K. J. et al.; 17 C. M. Behav. Pharmacol. 681-689 (2006); The 30 mg/kg dose of 5,6-Dibromo-N,N-dimethyl-tryptamine possessed both anxiolytic and antidepressant properties by attenuating separation distress vocalizations in the anxiety phase and elevating separation distress vocalizations in the final 30 min of the depression phase of the model, respectively as shown in FIG. 2.

Figure 3A:
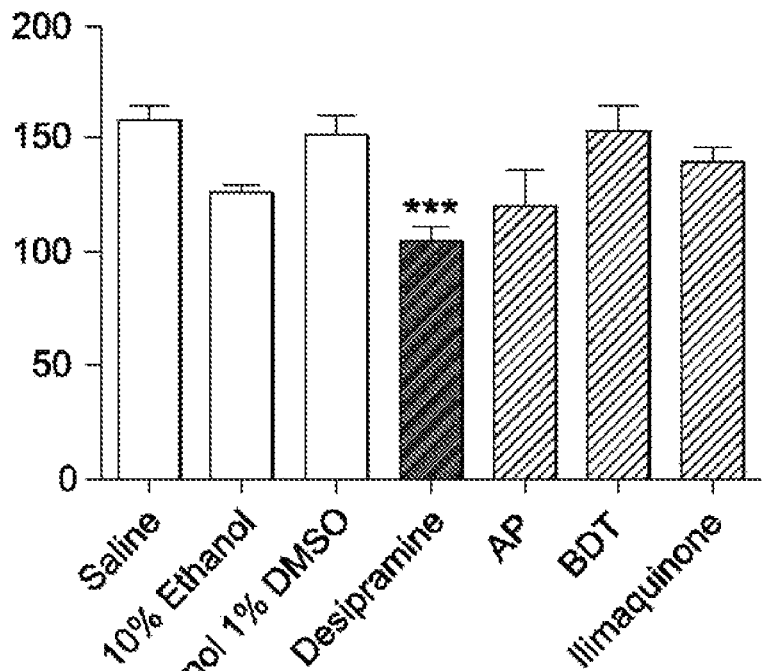
FIG. 3A. Shows effect of compounds 3 (AP), 2 (BDT) and 4 (ilimaquinone) in (A) FST.
Figure 3B:
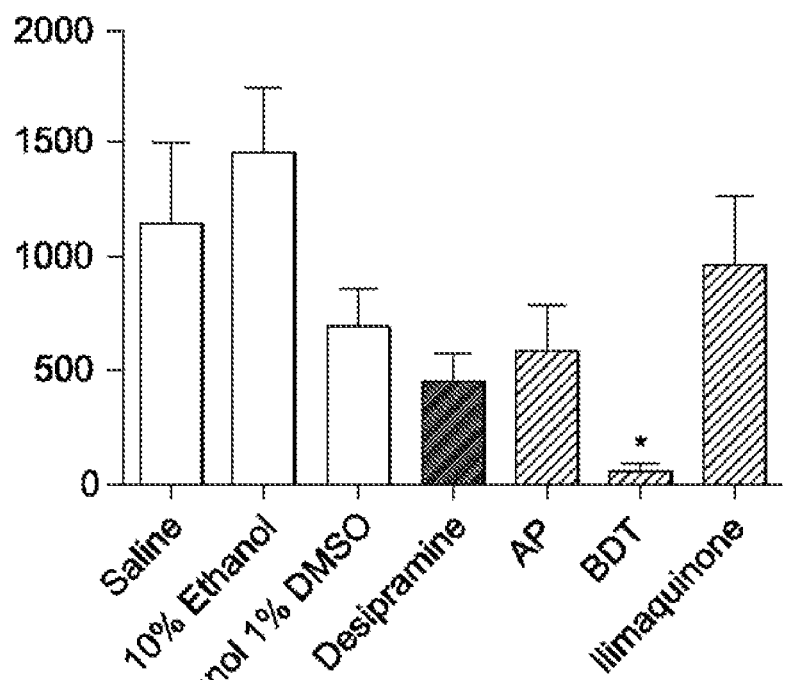
FIG. 3B. Shows effect of compounds 3 (AP), 2 (BDT) and 4 (ilimaquinone) in FST and locomotor activity test in male Swiss Webster mice. *p<0.05 and ***p<0.001 versus corresponding vehicle.

Interestingly, compound 2, differing from 1 only by one bromine atom, did not exhibit antidepressant-like activity, but instead showed a significant sedative effect (t=3.55; p<0.05) (FIG. 3B). Aplysinopsin (3) and ilimaquinone (4) did not show any significant antidepressant-like activity in the rodent swim test.

In order to confirm that reduction of immobility induced by the tested compounds is true and not a result of a nonspecific stimulant action in the FST, the effect on locomotor activity was determined, whereby a nonspecific stimulant action is reflected as a hyperlocomotive effect. Analysis of variance revealed an overall significant difference between the treatment groups (F[6; 38]=3.10, p<0.05). However, Bonferroni's multiple comparisons posthoc test revealed that there were no statistical differences between any of the tested compounds and their respective vehicle controls. Such results demonstrate that the observed antidepressant-like effect of 5,6-dibromo-N,N-dimethyltryptamine (1) is not associated with a stimulant action. In fact, I caused a nonsignificant trend toward decreasing locomotor activity, which would not account for its significant reduction of immobility time in the FST.

General Experimental Procedures. The 1H- and 13 C-NMR spectra were recorded in CDCl3, MeOD and DMSO-d6 on a NMR spectrometer operating at 400 MHz for 1H and 100 MHz for 13 C-NMR. The MS spectra were measured using a Bioapex FTESI-MS with a Bruker microTOF instrument. TLC was carried out on precoated silica gel G254 or aluminium oxide ALOX-100 UV254 (500 μm) plates. HPLC was carried out on a Waters system with a Waters 2487 detector.

Animal material, *S. aurea* was collected from the Florida Keys in August 2005. The sponges were collected from shallow coral reef habitat between 6-24 m depth at Key Largo, Fla., July and August 2005. Voucher specimens have been deposited in the Natural History Museum, London (BMNH 2007.4.23.1 [University of Mississippi voucher 05FL-020 (3)]; BMNH 2007.4.23.2 [University of Mississippi voucher 05FL-027].

*V. rigida* was collected from shallow coral reef habitat between 3-21 m depth at Key Largo. Fla. Voucher specimens have been deposited in the Natural History Museum, London (BMNH 2007.4.23.3 [University of Mississippi voucher 05FL-020(2)]; BMNH 2007.4.23.4 [University of Mississippi voucher 05FL-089].

*S. cerebriformis* was collected from shallow coral reef habitat between 3-21 m depth at Key Largo, Fla. Voucher specimens have been deposited in the Natural History Museum. London (BMNH 2007.4.23.5 [University of Mississippi voucher 05FL-020(1)]; BMNH 2007.4.23.6 [University of Mississippi voucher 0505FL-161]. Taxonomical identification of sponges was completed by Dr. M. Kelly.

Extraction and Isolation. The sponge *S. aurea* was stored frozen until extracted. A sample of the sponge collected from Florida in November 2002 (35 g) was lyophilized, crushed, homogenized and then extracted with ethanol at room temperature. A second sample of sponge extract was obtained after grinding and exhaustive extraction with ethanol and yielded 21 g. TLC analysis indicated that the extracts contained various minor alkaloids. The extracts were subjected to silica gel vacuum liquid chromatography and eluted in order, with hexane (100%), hexane-acetone (9:1, 3:1, 1:1), acetone (100%), chloroform-methanol (1:1) and methanol (100%). Altogether seven major fractions were collected and the elution of metabolites was monitored by TLC. Further work-up (column chromatography on silica gel) of fraction 1 gave 80 mg (0.36% dry weight) of aureol (8), fraction 2 gave 45 mg (0.2% dry weight) of 5,6-dibromo-N,N-dimethyltryptamine. 2'-Des-N-methylaplysinopsin (10, 1.5 mg. 0.0068% dry weight), 6-bromoaplysinopsin (6, 1.2 mg, 0.0054%) and makaluvamine O (9, 1 mg, 0.0045% dry weight) were obtained from fractions 3 and 4. Purification of fraction 5 gave thymine (2 mg) and uracil (3.5 mg). The compounds were identified by comparison of their spectral data (H-NMR, C-NMR, MS) with literature values.

Three kilograms of the frozen sponge *V. rigida* were extracted four times with 2000 mL of EtOH in a sonicator. The combined extracts were filtered and concentrated in vacuo until dried. The crude extract (211 g) was then subjected to vacuum-liquid chromatography using gradient solvent system from hexanes through acetone to methanol yielding 20 fractions. The acetone/methanol fraction (1:1) was further purified by flash column chromatography (C18 cartridge) with water-methanol solvent system yielding five fractions. Further purification of fraction 4 (H2O/MeOH 1:3) on HPLC C8 column (gradient from 100% H2O to 100% MeOH) yielded 740 mg (0.35% dry weight) of 5,6-dibromo-N,N-dimethyltryptamine (1). The compound was isolated as yellow amorphous solid and could be purified by repeated recrystallization from methanol and identified on basis of H-NMR, C-NMR and HRMS spectra. Further work-up of residue of the same fraction by silica gel preparative thin layer chromatography (chloroform/methanol 8:2) and HPLC (C8 columns, gradient from water to acetonitile) resulted in isolation of 0.1 mg makaluvamine O (9) and 0.3 mg of arborescidine C (5), identified with mass spectrometry and H-NMR analysis. Purification of fraction 3 on HPLC (C8 column, water to acetonitrile solvent gradient system) yielded 3 mg (0.00142% dry weight) of 5-bromo-N,N-dimethyltryptamine (2). Presence of this compound was confirmed with H-NMR. C-NMR and FIRMS.

A fraction eluted with 100% MeOH from the VLC silica column after further purification on C18 column yielded 5 fractions: further work up on water and MeOH fraction yielded 32.5 mg (0.0154% dry weight) of aplysinopsin (3), identified by comparison of the spectral data (H-NMR, C-NMR, HRMS) with literature values. Purification of the same fraction resulted in isolation of 1 mg (0.00047% dry weight) of 5,6-dibromoabrine (7) and 6-bromoaplysinopsin (6, 2.0 mg, 0.00094% dry weight). The fraction eluted with hexane/acetone 8:2 from VLC yielded small amounts of ilimaquinone (4, 5 mg. 0.00236% dry weight) and 2 mg (0.00094% dry weight) of aureol (8). The presence of these compounds was confirmed by TLC, MS and NMR analysis, comparing with standards.

Six kilograms (wet weight) of the frozen sponge *S. cerebriformis* were extracted exhaustively with EtOH in a sonicator. The combined extracts were filtered and concentrated in vacuo until dried. The crude extract (260 g) was then subjected to vacuum liquid chromatography using a gradient solvent system from hexanes through acetone to methanol yielding 20 fractions. Non polar fractions after purification yielded 2.5 g (0.9615% dry weight) of ilimaquinone (4) which was identified by comparison of H-NMR and C-NMR data with standard. Fractions eluted with methanol showed a characteristic pattern of dibrominated compound and the FIRMS comparison with the standard revealed the presence of 5,6-dibromo-N,N-dimethyltryptamine (1).

Locomotor Activity and the FST. To evaluate the isolated compounds for antidepressant-like activity, male Swiss Webster mice (Harlan, Indianapolis, Ind.) (25-30 g weight) were used. Animals were housed in groups of five with a 12 h light/12 h dark cycle. Food and water were provided at libitum. All procedures involving animals were performed as approved by the Institutional Animal Care and Use Committee of the University of Mississippi. Animals were randomly divided into groups (n=6-10/group). Each group was injected IP with either the compound (1-20 mg/kg), desipramine (20 mg/kg), or vehicle (saline, 10% ethanol or 10% ethanol/1% DMSO). Following injection, locomotor activity was monitored using an automated activity monitoring system (San Diego Instruments, San Diego, Calif.). Each mouse was placed in a Plexiglas enclosure and locomotor activity was recorded as the number of photobeam interruptions for 30 min after drug injection. The activity for the last ten min was quantified and analyzed. Immediately at the end of the locomotor session, individual mice were subjected to the FST. The mice were individually placed in a clear plastic cylinder (23 cm high, 10 cm internal diameter) filled with deionized water (8 cm high) at 25° C. The mice were recorded with a video camera (positioned at about 30 cm above the cylinder) for a total of 6 min. The total period of immobility during the last 4 min was timed by three independent observers. The mean immobility time was then calculated. A mouse was judged to be immobile when it remained afloat, making only minimal movements to keep its head above water.

Sulfka Chick Anxiety-Depression Model (SCADM) Test. Group housed white-leghorn cockerels (Cal-Maine W36) were tested at ages 5-6 days post-hatch. Chicks were placed in isolation into a 6 unit sound-attenuating apparatus containing video cameras and microphones 15 min after receiving injections of vehicle or 10, 20 or 30 mg/kg 5,6-dibromo-N,N-dimethyltryptamine. Vocalizations were recorded in 5-min blocks over a 120 min test period. The anxiety phase of the model is characterized by high rates of distress vocalizations during the first 5 min of the test period. The depression phase of the model is characterized by a reduced (approximately 50% of the initial rate) and stable rate of distress vocalizations during the 30-120 min period of the test session. All animal procedures were performed by the guidelines approved by the Institutional Animal Care and Use Committee.

For the FST, immobility times of the three independent rates were averaged for each mouse and data were analyzed using one way analysis of variance (ANOVA) followed by Bonferroni Multiple comparison posthoc tests to determine statistical differences from the corresponding vehicle control. Chick distress vocalization data were analyzed by two-way repeated measures ANOVA, one-way ANOVA and simple effects analyses with post-hoc comparisons conducted using Fisher's LSD test. p-Values less than 0.05 were considered statistically significant.

Example 2

Isolation and Identification of Marine Secondary Metabolites

Sponges of the order Verongida have been reported to yield a unique group of secondary metabolites characterized by the absence of terpenes and the presence of sterols and brominated compounds biogenetically related to tyrosine and tryptophan. Ciminello, P., et al, Chemistry of verongida sponges. Secondary Metabolite Composition of the Caribbean Sponge *Verongula gigantean* of 63 J. Nat. Prod. 263-66 (2000). We have collected and completed a preliminary evaluation of *Verongida* sponges from various parts of the world and successfully isolate twenty brominated indole and tyrosine derived alkaloids for a preliminary evaluation of their neuropharmacology.

As part of a brief preliminary evaluation sponges from Florida (*Verongida rigida, Smenospongia aurea* and *S. cerebriformis*) were extracted four times with 2000 mL of EtOH in a sonicator. The combined extracts were filtered and concentrated in vacuo until dried. The crude extracts were then subjected to vacuum-liquid chromatography using a gradient solvent system from hexanes through acetone to methanol yielding 20 fractions. The acetone/methanol fraction (1:1) was further purified by flash column chromatography ($C_{18}$ cartridge) with water-methanol solvent system yielding five fractions. Further purification of fraction 4 ($H_2O$/MeOH 1:3) on HPLC $C_8$ column (gradient from 100% $H_2O$ to 100% MeOH) yielded 740 mg of 5,6-dibromo-N,N-dimethyltryptamine. The compound was isolated as yellow amorphous solid and could be purified by repeated recrystallization from methanol and identified on basis of $^1$H-NMR, $^{13}$C-NMR and HRTOF-MS spectra. Purification of fraction 3 on HPLC ($C_8$ column, water to acetonitrile solvent gradient system) yielded 3 mg of 5-bromo-N,N-dimethyltryptamine. Presence of this compound was confirmed with $^1$H-NMR, $^{13}$C-NMR and HRMS. Further purification of polar VLC fractions on HPLC reversed phase (C8 and C18) columns led to the isolation of eight mg of veranamine (VR1) and 400 mg of 3-bromotyramine (216/218). The presence of known compounds was confirmed by TLC, MS and NMR analysis and comparison with the data from the literature.

Evaluation of binding affinity of isolated compounds to serotonin receptors. In vitro testing of isolated compounds was completed using a small panel of receptor binding assays and then validated in a comprehensive panel by the NIMH Psychoactive Drug Screening Program. Pharmacological and functional screening of isolated molecules was performed on cloned human or rodent CNS receptors, channels, and transporters. Hu, J-F., et al. New Antiinfective and Human 5-HT2 Receptor Binding Natural and Semisynthetic Compounds from the Jamaican Sponge *Smenospongia aurea*. 65 Jour. of Nat. Prod. 476-80 (2002).

The preliminary data from in vitro receptor binding assays showed that 5,6-dibromo-N,N-dimethyl tryptamine binds to 5-HT$_{2B}$ receptors with K$_i$=11 nM, to 5-HT$_6$ with K$_i$=48 nM and with lower affinity to 5-HT$_{2A}$ (K$_i$ 243 nM) and 5-HT$_{2C}$ (K$_i$ 187 nM). Aplysinopsin derivatives (6-bromoaplysinopsin, 6-bromo-2'-de-N-methylaplysinopsin and N-3'-ethylaplysinopsin) were reported to exhibit high-affinity and selective binding to human serotonin receptors: 5-HT$_{2A}$ and 5-HT$_{2C}$. N-3'-ethylaplysinopsin did not display selectivity to either of these two receptors (K$_i$ of 3.5 µM and 1.7 µM for 5HT$_{2C}$ and 5HT$_{2A}$ receptor respectively), 6-bromoaplysinopsin showed only small selectivity towards 5HT$_{2C}$ receptors (K$_i$ 0.33 µM and 2.0 µM for 5HT$_{2C}$ and 5HT$_{2A}$ receptor respectively), while 6-bromo-2'-de-N-methylaplysinopsin exhibited strong (40 fold) selectivity to 5HT$_{2C}$ receptors (K$_i$ 2.3 µM for 5HT$_{2C}$ and >100 µM for 5HT$_{2A}$).

In order to evaluate bioactive marine natural products for potential antidepressant activity, several compounds were identified that possess structural similarities to serotonin or antidepressant drugs. The selected compounds (aaptamine, isoaaptamine, 8,9-methylaaptamine, 5,6-dibromo-N,N-dimethyltryptamine, Veranamine (VR1), and 3-bromotyramine (216/218) possessed moderate affinities to serotonin receptors and were thus evaluated for antidepressant-like action in mice using the FST (FST). The FST animal model established by Porsolt has been the most extensively used test to predict antidepressant drug action. The test proved to be sensitive to all major classes of antidepressants whereby an antidepressant action is reflected by decreased immobility time exhibited by mice under forced swim conditions. Porsolt R D, et al. Behavioral Despair In Mice: A Primary Screening Test for Antidepressants, 229 Arch. Int. Pharmacodyn. 327-36 (1977). Compounds that showed promising antidepressant effect in the FST were further evaluated in the secondary tail suspension test (TST) to shed light on the potential therapeutic value as well as mechanism of antidepressant action. In order to control for false positives, as has been previously observed with psychostimulants, Cryan, J., et al. Assessing Substrates Underlying The Behavioral Effects Of Antidepressants Using The Modified Rat Forced Swimming Test. 29 Neurosci Biobehav Rev. 547-69 (2005) locomotor activity of the animals was monitored using an automated photobeam activity monitoring system. Lucki. I. The Forced Swimming Test As A Model For Core And Component Behavioral Effects Of Antidepressant Drugs. 8 Behav. Pharmacol. 522-32 (1997).

Figure 4A:
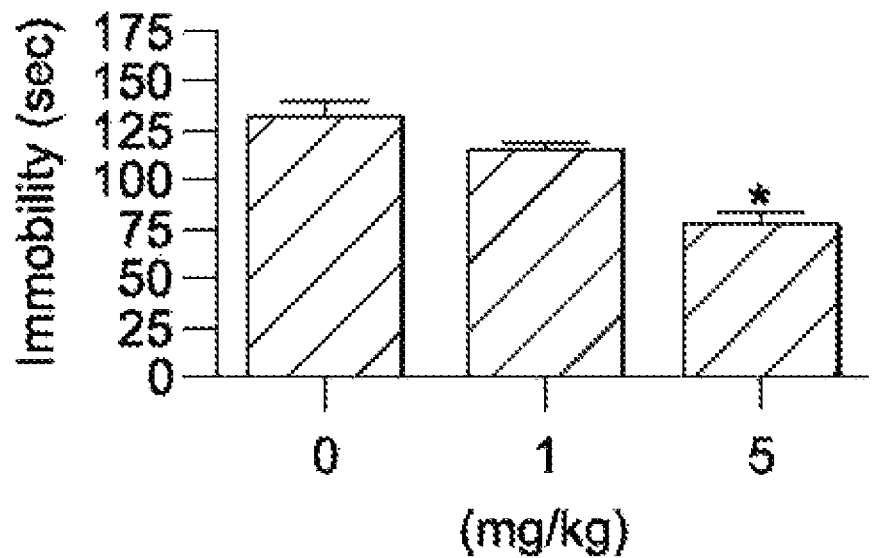
FIG. 4A. Shows dose dependent reduction of immobility (sec) in mouse FST by citalopram.
Figure 4B:
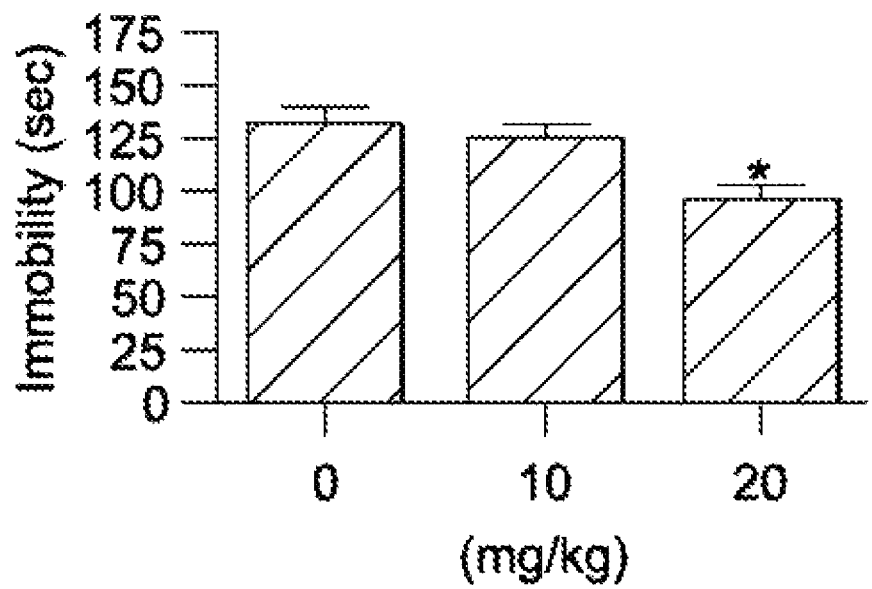
FIG. 4B. Shows dose dependent reduction of immobility (sec) in mouse FST by desipramine.

As shown in FIGS. 4A and 4B, respectively, the SSRI antidepressant positive control, citalopram and the TCA positive control desipramine both dose-dependently reduced immobility time of Swiss Webster mice in the FST. Dunnett's post-hoc comparisons of citalopram confirmed that the 40% reduction in immobility time produced by the 5 mg/kg dose differed significantly from the saline vehicle (p<0.01). Post-hoc comparisons of desipramine confirmed that the 27% reduction in immobility time produced by the 20 mg/kg dose differed significantly from the saline vehicle (p<0.01).

Figure 5A:
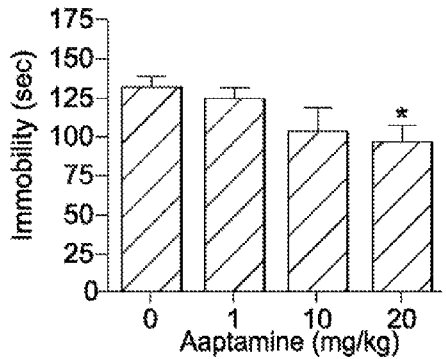
FIG. 5. Shows effect of aaptamine (A), isoaaptamine (B), and 8,9-demethylaaptamine (C) on immobility time in mouse FST.
Figure 5B:
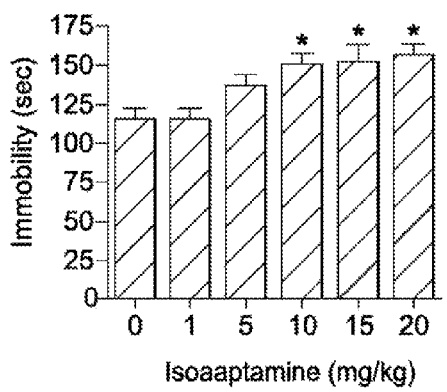

Evaluation of the isolated marine secondary metabolites revealed that aaptamine (p<0.05) dose-dependently reduced immobility time in the FST (FIG. 5A). Post-hoc comparisons of individual doses to the vehicle control showed that aaptamine differed significantly at only the 20 mg/kg dose (p<0.05), at which it produced a 36% reduction in immobility time, indicative of an antidepressant-like action. In contrast, isoaaptamine (p<0.01) significantly increased immobility time in a dose-dependent manner (FIG. 5B). Post-hoc comparisons of individual doses to vehicle control showed that isoaaptamine at 10 mg/kg (p<0.05), 15 mg/kg, and 20 mg/kg significantly increased immobility as compared to the control. Such increases in immobility might suggest a sedative action of the compound.

Figure 6A:
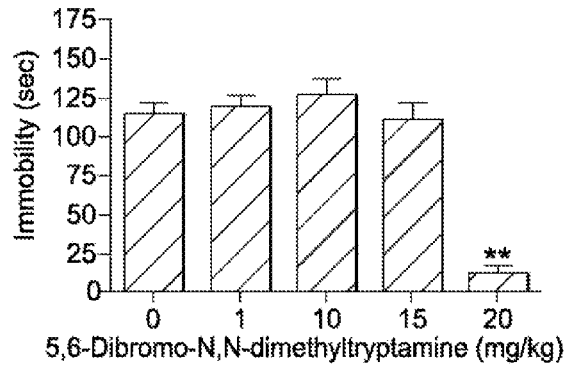
FIG. 6. Shows effect of 5,6-dibromo-N,N-dimethyltryptamine (A), manzamine A (B), and compound 3-bromotyramine (C) on immobility time in mouse FST.
Figure 6B:
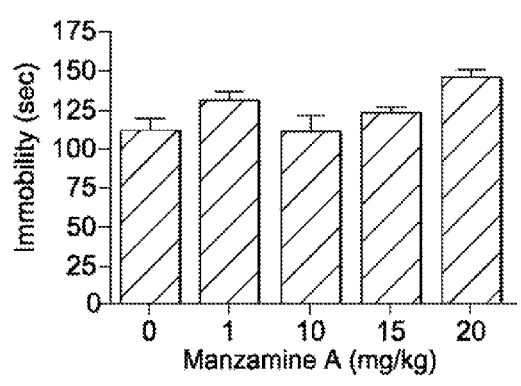
Figure 5C:
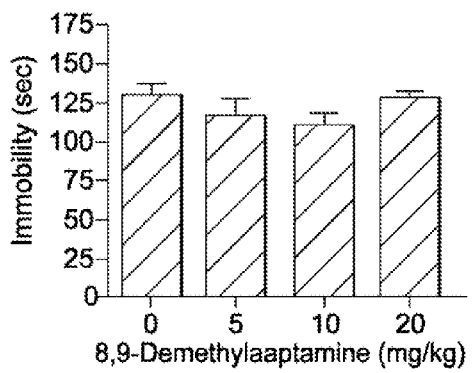
Figure 6C:
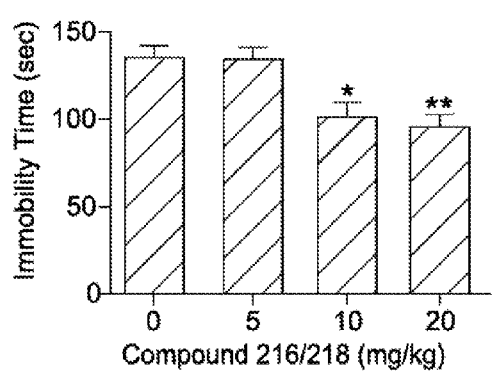
Figure 7A:
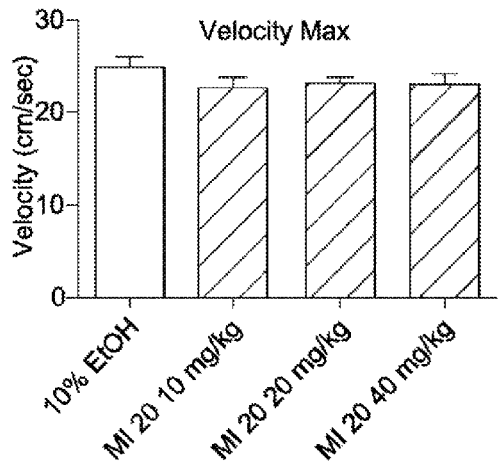
FIG. 7. Shows FST and locomotor activity test results for 5-bromo-N,N-dimethyltryptamine.
Figure 7B:
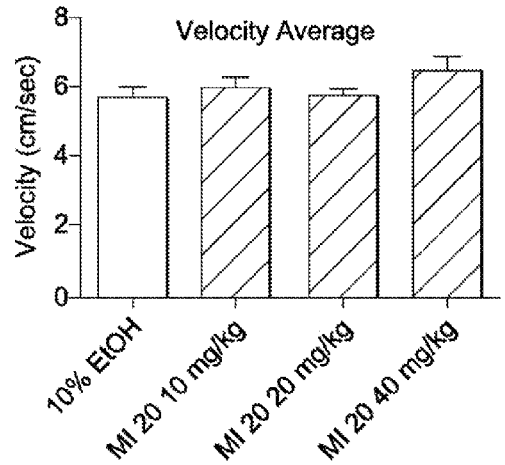
Figure 7C:
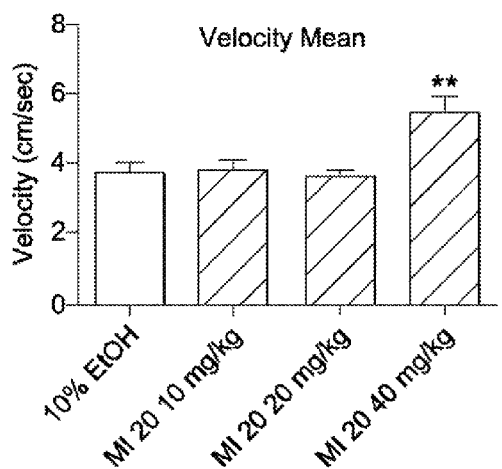
Figure 7D:
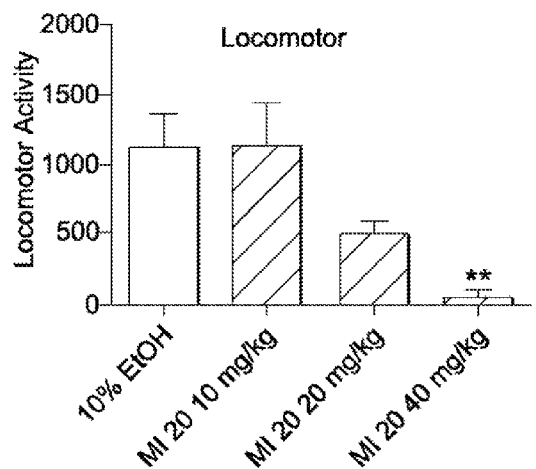
Figure 7E:
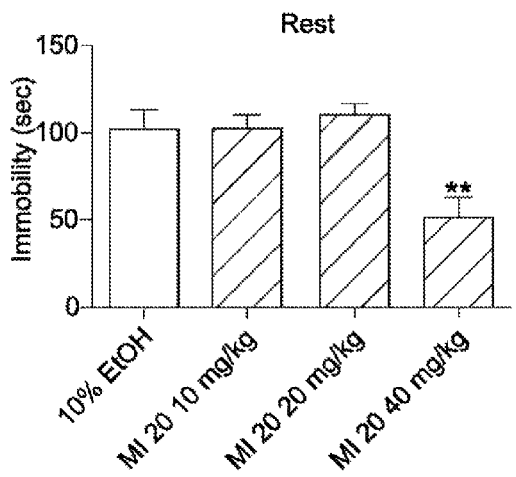
Figure 7F:
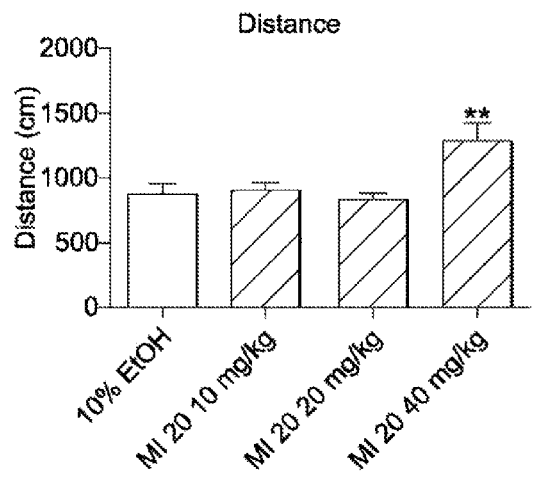
Figure 7G:
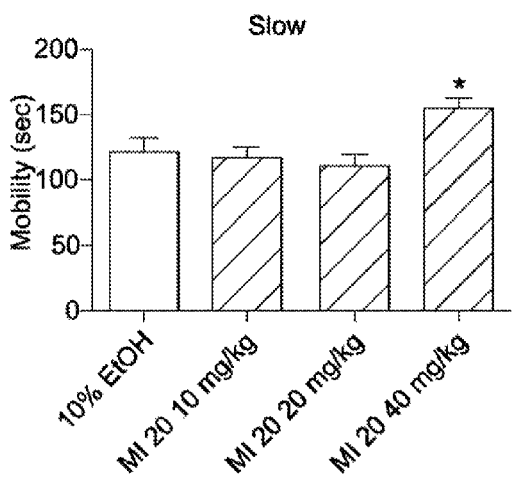
Figure 7H:
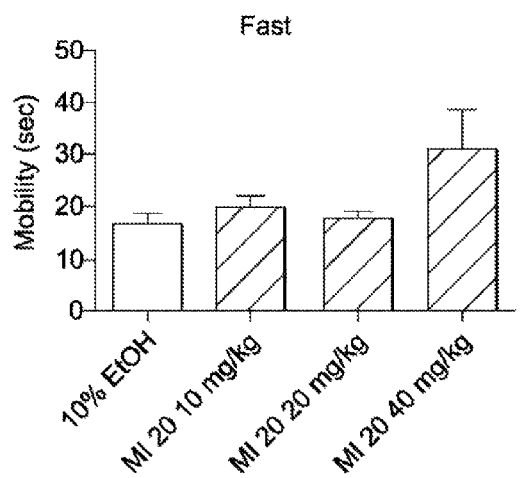
Figure 8:
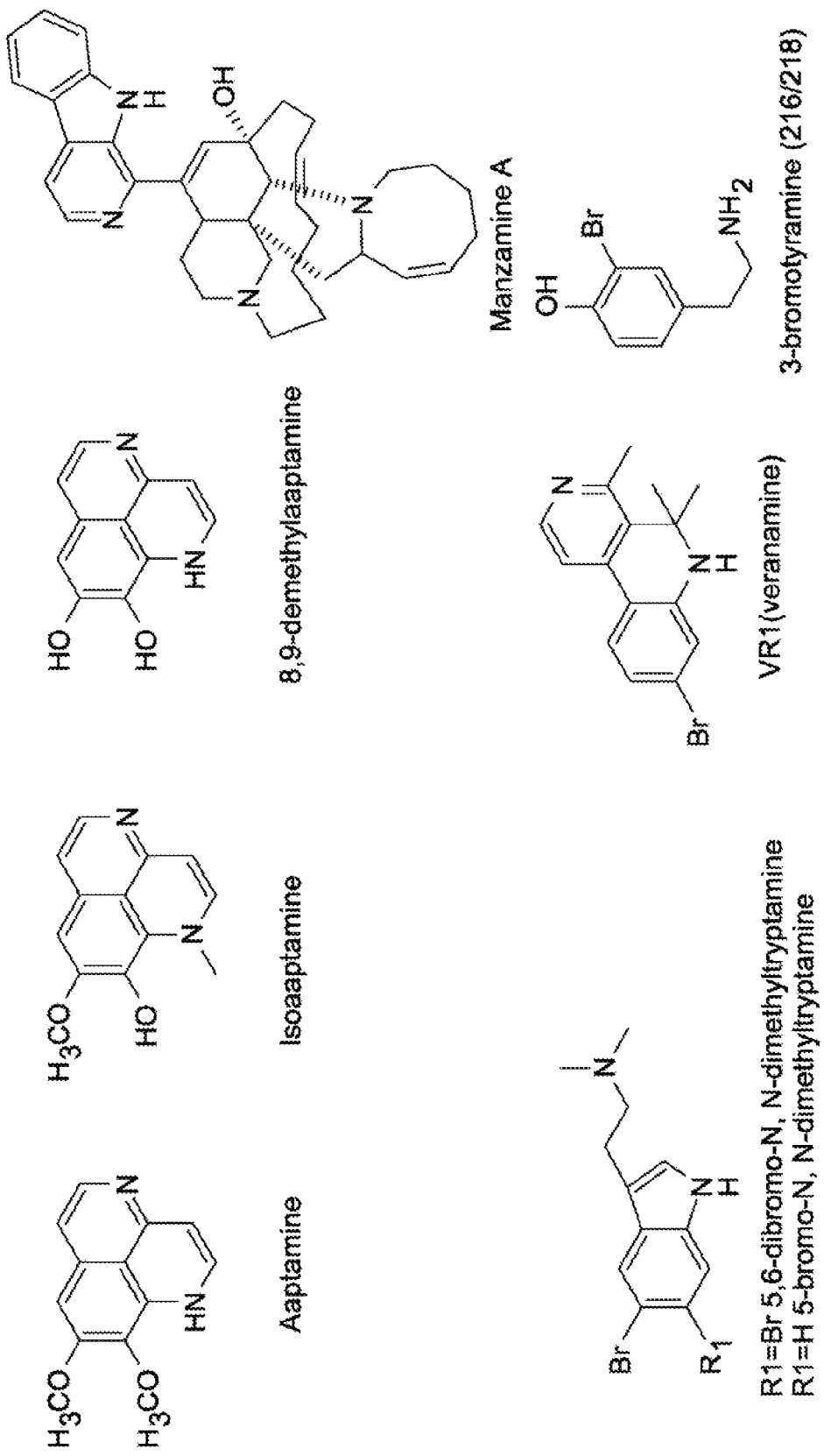
FIG. 8. Shows natural and derived marine compounds tests for activity in the animal models.

Neither the semisynthetic aaptamine derivative 8,9-demethylaaptamine (FIG. 5C), nor manzamine (FIG. 6B) showed any significant effect in the FST. On the other hand, the novel compound 5,6-dibromo-N,N-dimethyltryptamine exerted a significant antidepressant-like action at only the 20 mg/kg dose (p<0.01) (FIG. 6A). Compound 216/218 exhibited a dose dependent reduction in immobility in the FST, with the antidepressant like action significantly different from the vehicle control at both the 10 and 20 mg/kg dose (p<0.05 and p<0.01, respectively) (FIG. 6C).

Based on the data collected from the FST, the antidepressant action of aaptamine, 5,6-dibromo-N,N-dimethyltryptamine, and 3-bromotyramine was examined in the mouse tail suspension test (TST), another model highly predictive of antidepressant action. Similar to the FST, this test depends on the depressive behavior elicited by the animals when placed in an inescapable situation, in this case suspending the animal by its tail. Male DBA2/J mice were used for this test.

Figure 9A:
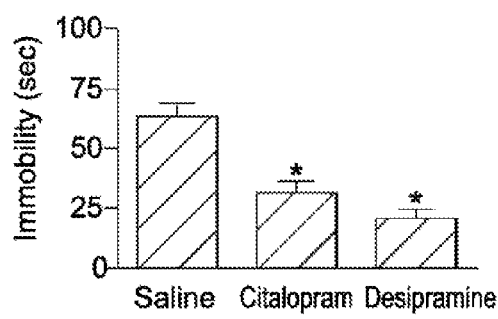
FIG. 9. Shows effect of (A) the antidepressants citalopram (5 mg/kg) and despramine (20 mg/kg), (B) aaptamine, (C) 5,6-dibromo-N,N-dimethyltryptamine, and (D) compound 3-bromotyramine on immobility time in mouse tail suspension test.
Figure 9B:
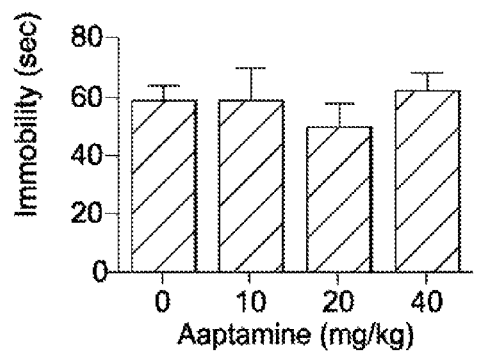
Figure 9C:
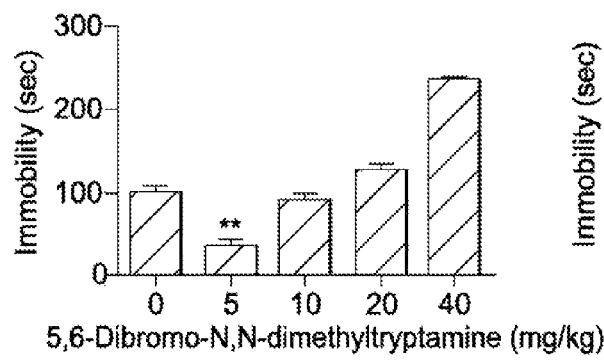
Figure 9D:
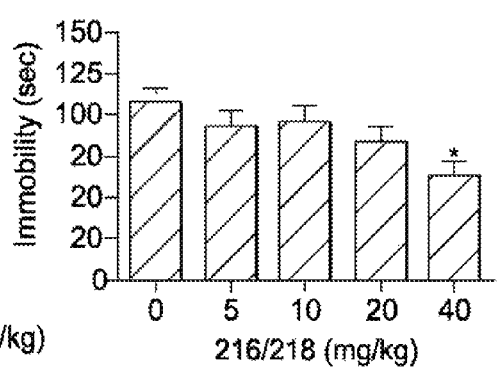

A drug producing an antidepressant-like action will decrease the immobility time exhibited by the animals. As shown in FIG. 9A, both desipramine (20 mg/kg. i.p.) and citalopram (5 mg/kg, i.p.) caused a significant reduction in immobility in the tail suspension test and hence served as a positive control in subsequent tests. Interestingly, the profile of antidepressant action exerted by the marine compounds in the TST seemed quite different from that revealed by the FST. While aaptamine showed antidepressant-like action in the FST, it failed to significantly reduce immobility in the TST (FIG. 9B). On the other hand, the 5,6-N,N-dimethyltryptamine showed a strong antidepressant-like action at the 5 mg/kg dose only. In fact, higher doses seem to increase immobility time (FIG. 9C). Similar to the FST, compound 216/218 showed a significant antidepressant action. However, such effect was only evident at the 40 mg/kg dose (compared to 10 and 20 mg/kg dose in the FST) (FIG. 9D).

Effect of select compounds on locomotor activity. Since reductions in immobility time is the primary criterion to assess antidepressant like activity in both the FST and TST, it is crucial to confirm that the effects observed in both tests are not attributed to specific stimulant action of the tested compounds, which would be reflected as enhancement of the locomotor activity. Accordingly, the effect of tested compounds on locomotor activity was evaluated using an automated activity monitoring system.

Figure 10A:
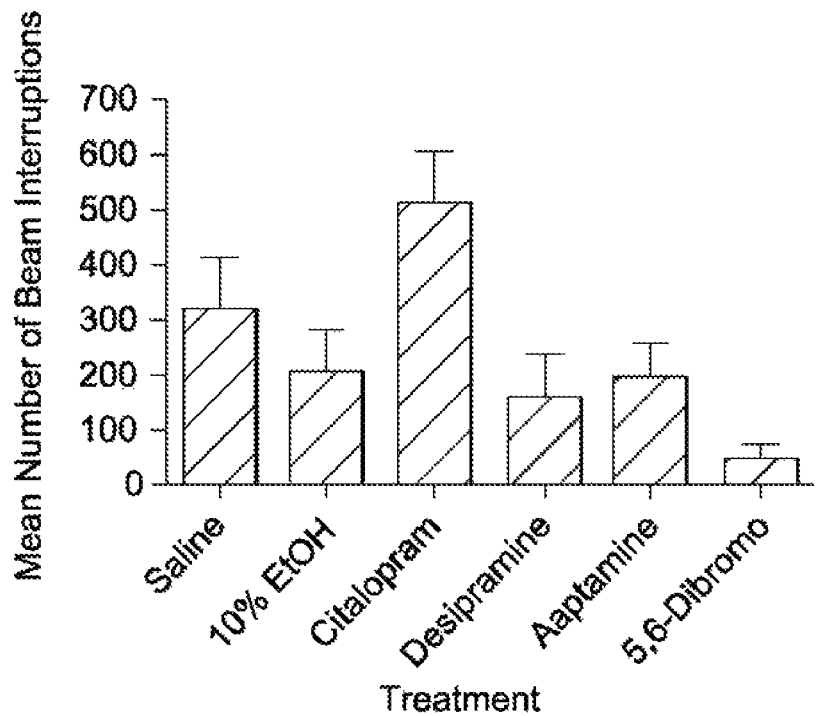
FIG. 10. Shows effect on locomotor activity of compounds producing significant effects in the FST (A) and tail suspension test (B).
Figure 10B:
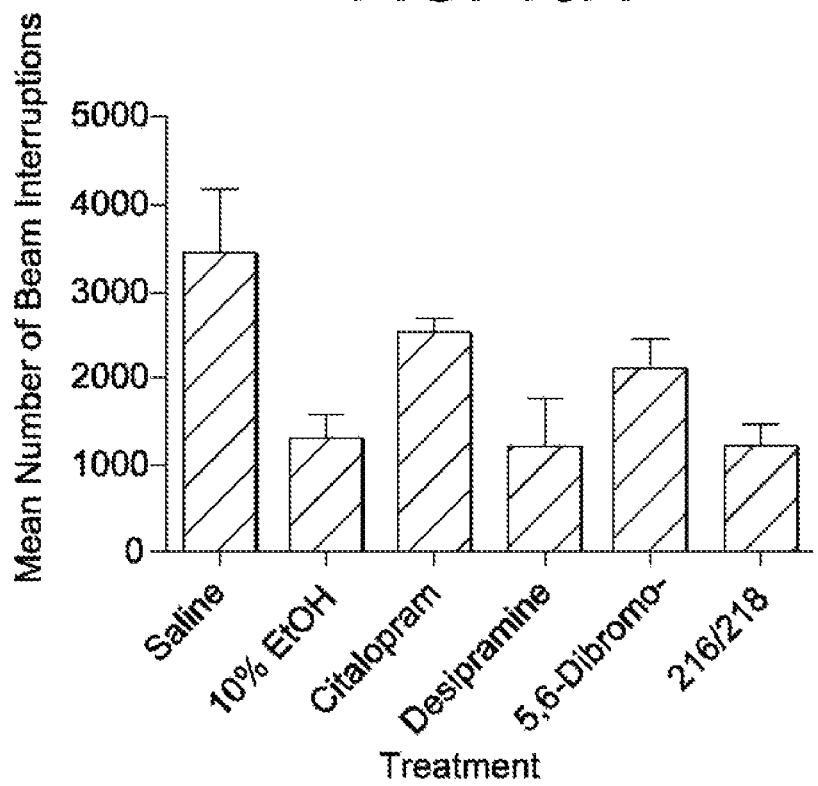
Figure 11:
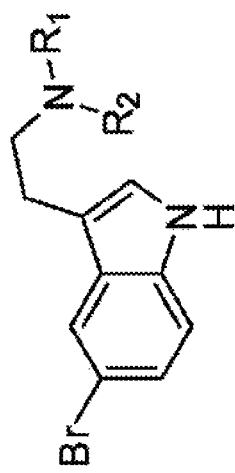
FIG. 11. Shows various compositions isolated or derived from marine natural products.
Figure 11:
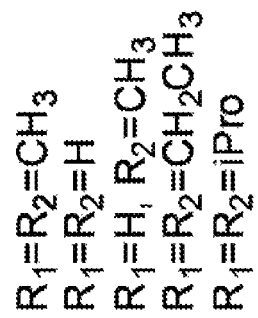
Figure 11:
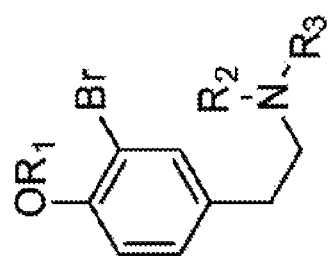
Figure 11:
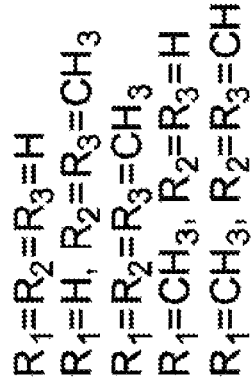
Figure 11:
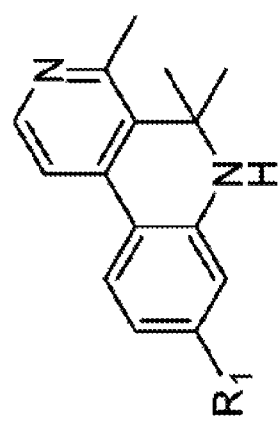
Figure 11:
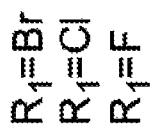

For the Swiss Webster mice, analysis of variance revealed a significant difference between the treatment groups. However, Tukey's post-hoc tests confirmed that there were no statistical differences between the vehicle controls, or compounds from their respective vehicle controls (FIG. 10A). Compared to their saline vehicle control, there was no significant difference in locomotor activity for citalopram 5 mg/kg, desipramine 20 mg/kg, or aaptamine 20 mg/kg. Likewise, there was no statistically significant difference for 5,6-dibromo-N,N-dimethyltryptamine 20 mg/kg compared to its 10% EtOH vehicle control, although it produced a noticeable reduction in activity (FIG. 10A). In DBA2/J mice, the pattern of responding in the locomotor studies was similar to that observed in the Swiss Webster mice (FIG. 10B). Analysis of variance revealed that there was no significant difference between the treatment groups. Similarly, compound 216/218 did not alter the locomotor activity of either Swiss Webster or DBA2/J mice. It is thus evident that the drug/dose combinations that produced antidepressant-like effects in both the FST and TST were not associated with confounding stimulant effects effect of select compounds in chick anxiety/depression model:

Example 3

*V. rigida*, collected in Florida Keys, was extracted exhaustively with ethanol. The crude extract was reduced in volume and fractionated on silica gel column by vacuum liquid chromatography technique using gradient of solvents from hexane to methanol. Polar fractions were purified on reverse phase C18 cartridge by flash column chromatography and C8 HPLC column to yield 8 mg of the new alkaloid veranamine (VR1). The FIRMS of the compound showed two peaks of nearly the same intensity for the molecular ion peak at m/z 303-305 [M+H], which indicates presence of one bromine atom. The suggested molecular formula was therefore $C_{15}H_{15}BrN_2$ which was in agreement with NMR data. The UV spectrum showed absorption maximum at λ 204 nm. The IR spectra showed peaks at 3422 cm$^{-1}$, 2331 cm$^{-1}$, 1634 cm$^{-1}$ and 798 cm$^{-1}$.

The carbon NMR data indicated the presence of aromatic rings (10 signals in the aromatic region in $^{13}$C-NMR), confirmed by the $^1$H NMR spectrum, which showed 5 signals in the downfield region. Proton NMR spectrum contained signals in the upfield region corresponding to three methyl groups (☐ 1.62 integrated for 6 protons and ☐ 2.69 integrated for 3 protons). Detailed $^{13}$C and $^1$HNMR data. The structure assignment was completed using HMBC and COSY correlations. Veranamine was identified as (8-bromo-4,5,5-trimethyl-5,6-dihydrobenzo[c][2,7]naphthyridine). VR1 is depicted by the formula:

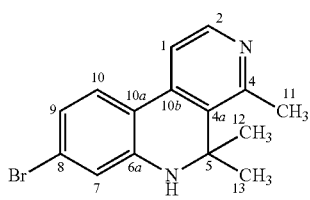

Figure 12A:
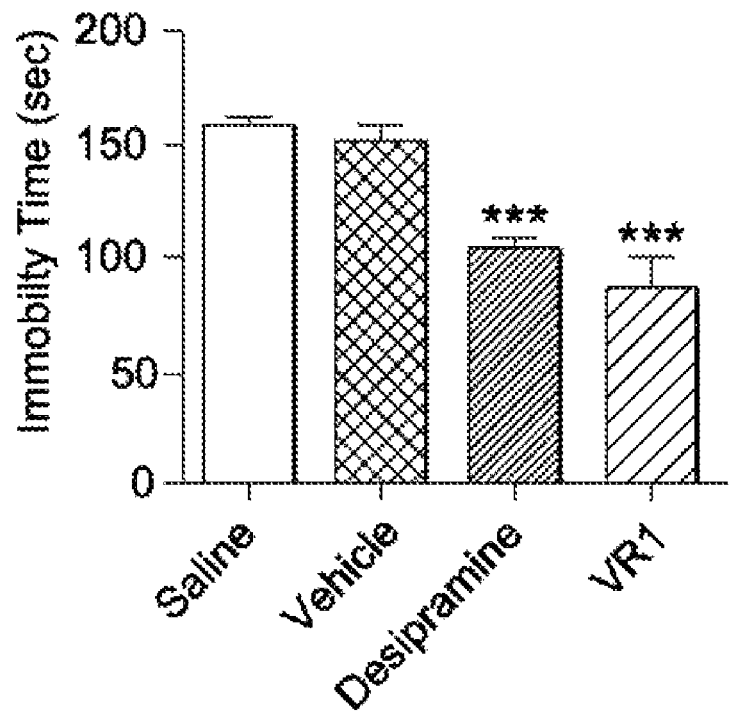
FIG. 12. Shows the effect of veranamine (20 mg/kg, i.p.) on A. immobility time in mouse forced swim test and B. locomotor activity in Swiss Webster mice compared to desipramine (20 mg/kg).
Figure 12B:
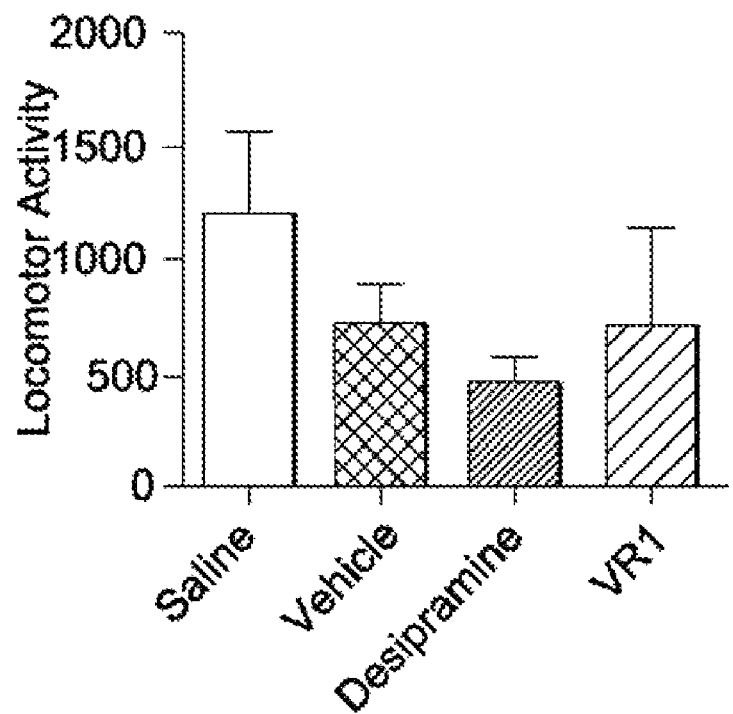

The compound was not active against HCV/HIV-1 and *Mycobacterium tuberculosis*. Considering the unusual ring system sharing common features with cannabinoids and tryptophan (serotonin) we tested the compound for possible antidepressant activity using a forced swim test. Veranamine showed potent antidepressant activity at the dose of 20 mg/kg, i.p. decreasing the immobility time significantly as compared to the control treatment desipramine. (20 mg/kg. i.p.) (FIG. 12A). A locomotor activity test was performed to exclude the possibility of nonspecific stimulant action that could create false-positive read out of FST (FIG. 12B). These results clearly showed that antidepressant activity of veranamine is not the consequence of its stimulant activity.

We claim:

1. A pharmaceutical formulation comprising a compound as depicted in formula (II), wherein (II) is as follows:

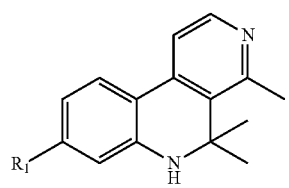

and a pharmaceutically acceptable carrier or a pharmaceutically acceptable excipient, wherein $R_1$=Br, Cl, I or F.

2. A pharmaceutical formulation comprising the compound of formula (IV) and a pharmaceutically acceptable carrier or a pharmaceutically acceptable excipient

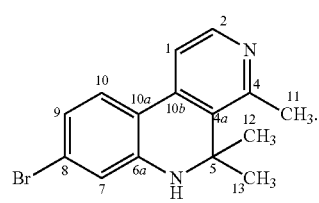

* * * * *